US00PP33238P2

(12) United States Plant Patent
Van Swieten

(10) Patent No.: US PP33,238 P2
(45) Date of Patent: Jul. 6, 2021

(54) ***PHALAENOPSIS* ORCHID PLANT NAMED 'PHALGUSWHA'**

(50) Latin Name: ***Phalaenopsis* hybrid**
Varietal Denomination: PHALGUSWHA

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/060,471

(22) Filed: Oct. 1, 2020

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGUSWHA', particularly characterized by white flowers with greenish-yellow and white lips, concave flower shape in lateral view, a compact plant, and is propagated by meristem tissue culture, is disclosed.

3 Drawing Sheets

Genus and species: *Phalaenopsis* hybrid.
Variety denomination: 'PHALGUSWHA'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGUSWHA'.

The new *Phalaenopsis* plant is a product of a planned breeding program conducted by the inventor in Bleiswijk, the Netherlands. The objective of this breeding program was to create a new *Phalaenopsis* plant with white flowers and greenish-yellow and white lips, suitable for potted plant production.

The new *Phalaenopsis* plant 'PHALGUSWHA' is a result of cross-pollination made by the inventor in April 2010 in Bleiswijk, the Netherlands, of the proprietary female, or seed parent, *Phalaenopsis* hybrid 'PHALCARDOK' (U.S. Plant Pat. No. 25,447) with the proprietary male, or pollen parent, *Phalaenopsis* hybrid '23312-03' (unpatented).

The new *Phalaenopsis* was selected by the inventor as a single plant within the progeny of the stated cross-pollination in a controlled greenhouse in Bleiswijk, the Netherlands, in February 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2390), by Applicant who obtained the subject matter disclosed directly from the inventor. 'PHALGUSWHA' has not been made publicly available or sold anywhere in the world prior to the effective filing date of this application with the exception of sales or disclosures made one year or less before the effective filing date of this claimed invention by Applicant who obtained 'PHALGUSWHA' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGUSWHA' as a new and distinct variety of *Phalaenopsis* plant:

1) White flowers with greenish-yellow and white lips;
2) Flower shape in lateral view is concave; and
3) Plant is compact.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2020. Colors in the photographs may differ from the color values cited in the detailed botanical description, which accurately describe the actual colors of the new variety.

DESCRIPTION OF THE NEW VARIETY

Figure 1:
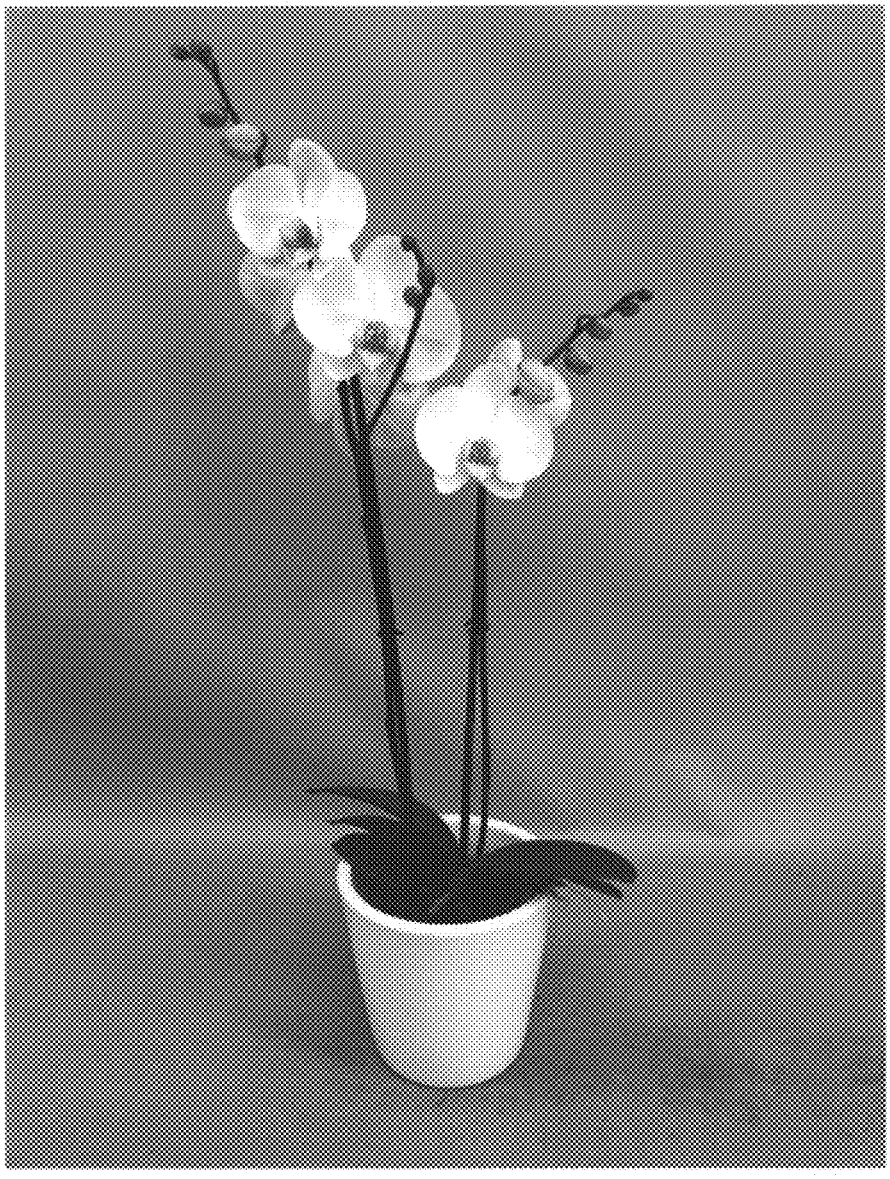
FIG. 1 shows the overall plant habit, including blooms, buds, and foliage of 'PHALGUSWHA'.
Figure 2:
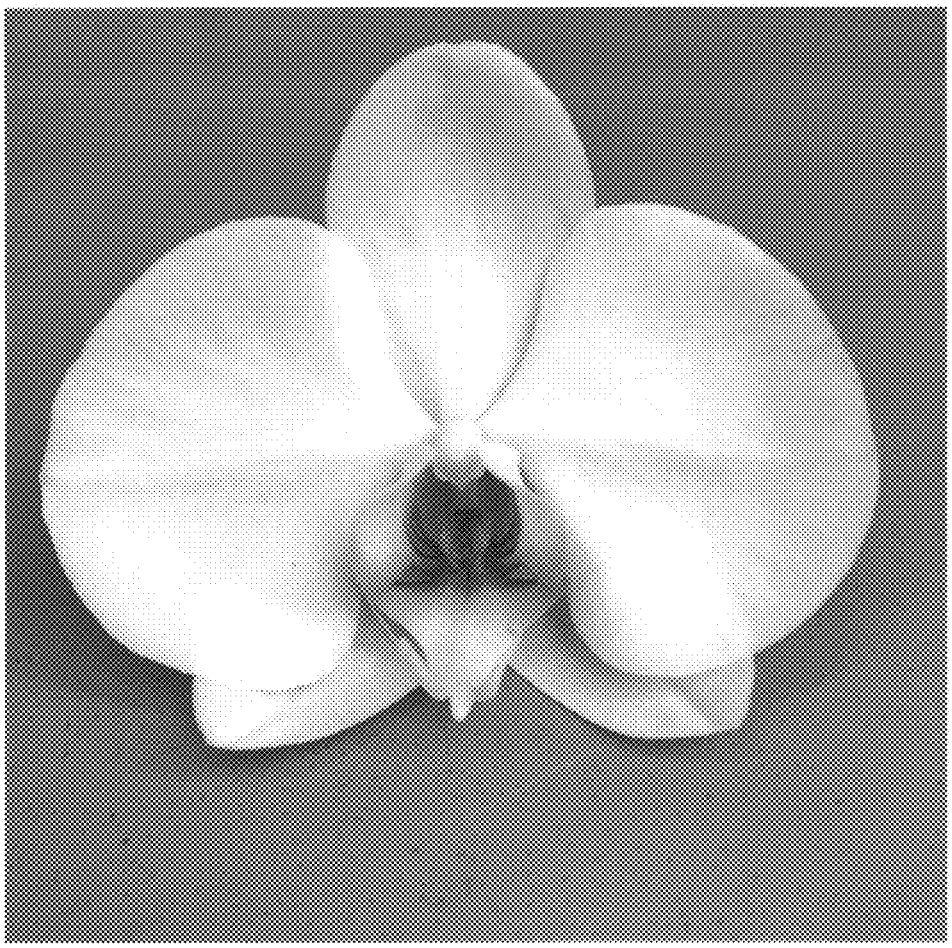
FIG. 2 shows a close-up of a flower of 'PHALGUSWHA'.
Figure 3:
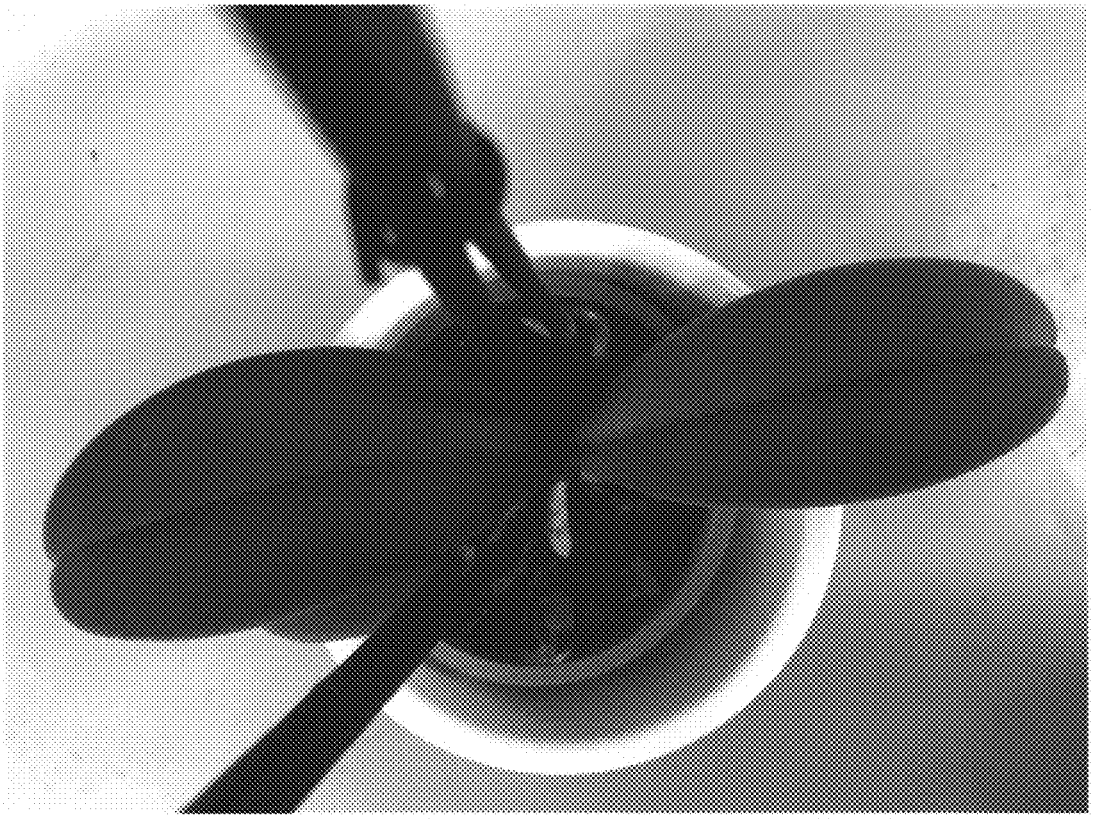
FIG. 3 shows an overhead view of the leaves of 'PHALGUSWHA'.

The following detailed description sets forth the distinctive characteristics of 'PHALGUSWHA'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGUSWHA'.

Parentage:

*Female parent*.—*Phalaenopsis* cultivar 'PHALCARDOK' (U.S. Plant Pat. No. 25,447).

*Male parent*.—*Phalaenopsis* cultivar '23312-03' (unpatented).

Propagation:

*Type*.—Meristem tissue culture.

Roots:

*Root description*.—Greyed-green (something between RHS 190B and 190C) colored roots with branching lateral roots having yellow-green (something in between RHS 144A and 144B) with a hint of dark purplish-red (RHS N79B) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height (from soil level to top of inflorescence)*.—Approximately 49.0 cm to 54.0 cm.

*Width (measured from leaf tips)*.—About 24.0 cm to 26.0 cm.

*Vigor*.—Strong.

Leaves:

*Mature leaves*.—Quantity per plant: 6 to 7 leaves are produced before flowering. Length (fully expanded): 12.0 cm to 14.0 cm. Width: 5.5 cm to 6.5 cm. Position of the broadest part of the leaf: At the middle. Shape: Oblong. Base shape: Moderately to slightly elongated. Apex: Emarginated unequal. Leaf blade angle with the petiole (measured from the horizontal position): Between 15 degrees and 30 degrees. Leaf margin: Entire. Color: Upper surface: RHS 146A. Lower surface: RHS 146B with a touch of RHS N77A. Texture (both upper and lower surfaces): Smooth. Thickness: 2.3 mm to 2.8 mm. Variegation: Absent. Venation: Pattern: Parallel. Color of the midvein: Upper surface: RHS 146A. Lower surface: RHS 146B with a touch of RHS N77A.

Peduncle:

*Quantity per plant*.—1 to 2.

*Number of flowers per peduncle*.—7 to 10.

*Length*.—49.0 cm to 54.0 cm.

*Diameter*.—4.0 mm to 5.0 mm.

*Strength*.—Strong.

*Aspect*.—Upright to slightly pendent.

*Texture*.—Smooth.

*Color*.—Mix of brown (RHS 200B) and green (RHS 146C).

*Internode length*.—3.0 cm to 4.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 160.0 mm to 200.0 mm.

*Flowering time*.—First flowers can be expected 10 to 11 months after planting in a 12-cm pot.

*Flower*.—Height: 80.0 mm to 85.0 mm. Diameter: 90.0 mm to 95.0 mm. Depth of lip: 25.0 mm to 27.0 mm.

*Flower longevity*.—On the plant: 10 to 12 weeks.

*Flower shape*.—Concave.

*Fragrance*.—Absent.

*Flower bud*.—Average size: Medium. Length: 28.0 mm to 30.0 mm. Width: 26.0 mm to 28.0 mm. Shape: Egg shaped. Color: Yellow-green (RHS 145C) with a touch of diluting purplish-red (RHS N77B).

*Petals*.—Arrangement: Open/free. Shape: Semi-circular. Apex: Rounded asymmetric. Margin: Weakly undulated. Length (from base to tip): 43.0 mm to 45.0 mm. Width: 54.0 mm to 56.0 mm. Position of the broadest part of the petal: Toward the base. Color (when fully opened): Upper surface: Basic color: White (RHS NN155C). Over color: Absent. Lower surface: Basic color: White (RHS NN155C). Over color: Very light purple midvein (RHS 76B) and hint of light yellow-green (RHS 145D) at the middle. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 45.0 mm to 47.0 mm. Width: 31.0 mm to 33.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Hint of light purple (something in between RHS 76A and 76B) and yellow-green (RHS 145A). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse asymmetric. Margin: Entire. Length (from base to tip):

46.0 mm to 48.0 mm. Width: 27.0 mm to 29.0 mm. Position of the broadest part of the lateral sepals: Toward the base. Color (when fully opened): Upper surface: Basic color: White (RHS NN155C). Over color: Light yellow-green (something in between RHS 145C and 145D) at the base. Lower surface: Basic color: White (RHS NN155C). Over color: Light yellow-green (RHS 145C); diluting dark purplish-red midvein (RHS N79C) toward the tip. Number of spots and stripes on the lateral sepals (upper surface): None. Color of spots and stripes on the lateral sepals (upper surface): None. Density of netting of the lateral sepals (upper surface): None. Color of the netting (upper surface): Not applicable.

*Labellum* (*lip*).—Whiskers: Present. Length of whiskers: 28.0 mm to 30.0 mm. Color of whiskers: Yellow (RHS 9A) at the base; white (RHS NN155C) with greenish-yellow tips (RHS 6B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 20.0 mm to 22.0 mm. Width: 15.0 mm to 17.0 mm. Color: Upper surface: Greenish-yellow (something in between RHS 151B and 5A) toward margin on one side; white (RHS NN155C) toward the margin on the other side. Lower surface: Greenish-yellow (something in between RHS 151B and 5A) toward margin on one side; white (RHS NN155C) toward the margin on the other side. Number of spots and stripes on the lateral lobe (upper surface): Few stripes at the base. Color of spots and stripes on the lateral lobe (upper surface): RHS 178A and 165C. Density of netting of the lateral lobe (upper surface): None. Color of the netting (upper surface): Not applicable.

*Apical lobe*.—Shape: Triangular. Margin: Entire. Length: 21.0 mm to 23.0 mm. Width: 26.0 mm to 28.0 mm. Color: Upper surface: Red margin (RHS 178A) at the base; greenish-yellow (something in between RHS 151B and 1A) toward wings; white (RHS NN155C) toward whiskers. Lower surface: Red margin (RHS 178A) at the base; greenish-yellow (something in between RHS 151B and 1A) toward wings; white (RHS NN155C) toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Medium. Height: 5.0 mm to 6.0 mm. Length: 5.0 mm to 6.0 mm. Width: 4.0 mm to 5.0 mm. Color: Yellow (RHS 15A); dotted (RHS 175A).

Reproductive organs:

*Column*.—Length: 8.0 mm to 10.0 mm. Diameter: 5.0 mm to 6.0 mm. Color: White (RHS NN155C).

*Pollinia*.—Quantity: 2. Diameter: 0.8 mm to 1.0 mm. Color: Orange (RHS 24A).

*Ovary*.—Length: 10.0 mm to 13.0 mm. Diameter: 2.2 mm to 2.4 mm.

*Pedicel*.—Length: 30.0 mm to 32.0 mm. Diameter: 2.6 mm to 2.8 mm. Texture: Smooth. Color: Hint of light brown (RHS 200C); yellow-green (RHS 145C) and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGUSWHA' differs from the female parent plant 'PHALCARDOK' (U.S. Plant Pat. No. 25,447) in that 'PHALGUSWHA' has smaller flowers and shorter leaves than 'PHALCARDOK'.

'PHALGUSWHA' differs from male parent plant '23312-03' (unpatented) in that 'PHALGUSWHA' has rounded petal apexes, whereas '23312-03' has emarginated petal apexes. Additionally, 'PHALGUSWHA' has shorter leaves than '23312-03'.

'PHALGUSWHA' is most similar to the commercial *Phalaenopsis* plants named 'PHALFOWIC' (U.S. Plant Pat. No. 29,245) and 'PHALFUBNE' (U.S. Plant Pat. No. 30,395). 'PHALGUSWHA' differs from the commercial variety 'PHALFOWIC' in that 'PHALGUSWHA' has emarginated dorsal sepal apexes, whereas 'PHALFOWIC' has obtuse dorsal sepal apexes. Additionally, 'PHALGUSWHA' has shorter and narrower leaves than 'PHALFOWIC'.

'PHALGUSWHA' differs from the commercial variety 'PHALFUBNE' in that 'PHALGUSWHA' has emarginated dorsal sepal apexes, whereas 'PHALFUBNE' has obtuse dorsal sepal apexes. Additionally, 'PHALGUSWHA' has smaller flowers and shorter and narrower leaves than 'PHALFUBNE'.

I claim:

1. A new and distinct variety of *Phalaenopsis* plant named 'PHALGUSWHA', substantially as described and illustrated herein.

* * * * *